(12) United States Patent
Lee et al.

(10) Patent No.: US 7,897,735 B2
(45) Date of Patent: Mar. 1, 2011

(54) COMPOUND HAVING THIOL ANCHORING GROUP, METHOD OF SYNTHESIZING THE SAME, AND MOLECULAR ELECTRONIC DEVICE HAVING MOLECULAR ACTIVE LAYER FORMED USING THE COMPOUND

(75) Inventors: Hyoyoung Lee, Daejeon (KR); Junghyun Lee, Gyeonggi-do (KR); Heeyoel Baek, Gyeongsangbuk-do (KR); Gyeong Sook Bang, Jeollabuk-do (KR); Jonghyurk Park, Daegu (KR); Nak-Jin Choi, Daegu (KR); Kun Jun, Daejeon (KR); Seung Rim Shin, Daejeon (KR)

(73) Assignees: Electronics and Telecommunications Research Institute (KR); Korea Research Institute of Chemical Technology (KR)

( * ) Notice: Subject to any disclaimer, the term of this patent is extended or adjusted under 35 U.S.C. 154(b) by 73 days.

(21) Appl. No.: 12/431,651

(22) Filed: Apr. 28, 2009

(65) Prior Publication Data

US 2009/0294762 A1 Dec. 3, 2009

Related U.S. Application Data

(62) Division of application No. 11/398,188, filed on Apr. 4, 2006, now Pat. No. 7,538,199.

(30) Foreign Application Priority Data

Sep. 26, 2005 (KR) .................. 10-2005-0089516

(51) Int. Cl.
*C07C 245/02* (2006.01)
(52) U.S. Cl. ............ 534/573; 549/29; 429/209; 544/136

(58) Field of Classification Search .................. None
See application file for complete search history.

(56) References Cited

U.S. PATENT DOCUMENTS 4,211,696 A * 7/1980 Baird et al. .................. 534/731
5,644,039 A * 7/1997 Hamprecht et al. .......... 534/573

FOREIGN PATENT DOCUMENTS

| GB | 2312436 A | * 10/1997 |
|---|---|---|
| JP | 56-161466 | 12/1981 |
| JP | 56161466 | * 12/1981 |

OTHER PUBLICATIONS

Jae-Hong Choi et al., "High fastness heterocyclic azo disperse dyes bearing ester functions", JSDC vol. 115, Jan. 1999 (pp. 32-37).

* cited by examiner

*Primary Examiner* — Sudhakar Katakam
(74) *Attorney, Agent, or Firm* — Blakely, Sokoloff, Taylor & Zafman

(57) ABSTRACT

Provided are an electron donor-azo-electron acceptor compound having a thiol-based anchoring group, a method of synthesizing the compound, and a molecular electronic device having a molecular active layer formed of the compound. The compound for forming a molecular electronic device includes an azo compound that has a dinitrothiophene group and an aminobenzene group having thiol derivatives. The compound forms a molecular active layer in the molecular electronic devices. The molecular active layer is self-assembled on an electrode using the thiol derivative in the azo compound as an anchoring group. The molecular active layer in the molecular electronic device forms a switching device switching between an on-state and an off-state in response to a voltage applied to electrodes or a memory device storing a predetermined electric signal in response to a voltage applied to the electrodes.

1 Claim, 20 Drawing Sheets

FIG. 5A

Current Data Parameters
NAME                sjh-h
EXPNO                   2
PROCNO                  1

F2 - Acquisition Parameters
Date_          500000
Time            18.18
INSTRUM         spect
PROBHO  5 mm QNP 1H
PULPROG          zg30
TD              32768
SOLVENT         COCl3
NS                 16
DS                  2
SMH          2073.563    Hz
FIDRES          0.087594 Hz
AQ           5.7015821   sec
RG               128
DM           174.000     usec
DE             7.93      usec
TE           300.0       K
D1           1.00000000  sec
P1            11.30      usec
DE             7.93      usec
SF01         300.2512851 MHz
NUC1            1H
PL1           -3.00      dB F2 - Processing Parameters
SI              32758
SF           300.2500142 MHz
MDW             EM
S58                 0
LB              1.00     Hz
GB                  0
PC              1.00

1D NMR plot parameters
CX             20.00     cm
F1P             8.113    ppm
F1           2436.01     Hz
F2P             0.155    ppm
F2             46.58     Hz
PPMCM           0.39791  ppm/cm
HZCM          119.47150  Hz/cm

FIG. 6A

Current Data Parameters
NAME          sjh-h
EXPNO            2
PROCNO           1

F2 - Acquisition Parameters
Date_         500000
Time           22.15
INSTRUM        spect
PROBHO  5 mm QNP 1H
PULPROG         zg30
TD             32768
SOLVENT       Aceton
NS                16
DS                 2
SMH         2620.545   Hz
FIDRES      0.079973   Hz
AQ          6.2521844  sec
RG               181
DM           190.800   usec
DE              7.93   usec
TE             300.0   K
D1         1.00000000  sec
P1             11.30   usec
DE              7.93   usec
SFO1       300.2512038 MHz
NUC1              1H
PL1            -3.00   dB F2 - Processing Parameters
SI             32758
SF         300.2500088 MHz
MDW               EM
S58                0
LB              1.00   Hz
GB                 0
PC              1.00

1D NMR plot parameters
CX             20.00   cm
F1P            7.794   ppm
F1          2340.09    Hz
F2P            0.036   ppm
F2            10.71    Hz
PPMCM         0.38791  ppm/cm
HZCM        115.46867  Hz/cm

FIG. 7A

```
Current Data Parameters
NAME              mjh-h
EXPNO                 2
PROCNO                1

F2 - Acquisition Parameters
Date_             500000
Time               21.21
INSTRUM            spect
PROBHO   5 mm QNP 1H
PULPROG             zg30
TD                 32768
SOLVENT           Aceton
NS                    16
DS                     2
SMH           2759.382    Hz
FIDRES        0.084210    Hz
AQ            5.9376116   sec
RG                   256
DM             181.200    usec
DE                7.93    usec
TE               300.0    K
D1          1.00000000    sec
P1               11.30    usec
DE                7.93    usec
SF01        300.2512759   MHz
NUC1                  1H
PL1              -3.00    dB F2 - Processing Parameters
SI                 32758
SF          300.2500088   MHz
MDW                   EM
S58                    0
LB                1.00    Hz
GB                     0
PC                1.00

1D NMR plot parameters
CX               20.00    cm
F1P              8.187    ppm
F1            2458.07    Hz
F2P              0.037    ppm
F2              11.18    Hz
PPMCM          0.40748    ppm/cm
HZCM         122.34440    Hz/cm
```

FIG. 8A

Current Data Parameters
NAME              mjh-h
EXPNO                 2
PROCNO                1

F2 - Acquisition Parameters
Date_            500000
Time              21.01
INSTRUM           spect
PROBHO   5 mm QNP 1H
PULPROG            zg30
TD                32768
SOLVENT           COCl3
NS                   16
DS                    2
SMH           2873.563  Hz
FIDRES        0.087694  Hz
AQ            5.7016821 sec
RG               161.3
DM             174.000  usec
DE                7.93  usec
TE               300.0  K
D1          1.00000000  sec
P1               11.30  usec
DE                7.93  usec
SF01       300.2513064  MHz
NUC1                1H
PL1              -3.00  dB F2 - Processing Parameters
SI                32758
SF         300.2500140  MHz
MDW                  EM
S58                   0
LB                1.00  Hz
GB                    0
PC                1.00

1D NMR plot parameters
CX               20.00  cm
F1P              8.101  ppm
F1             2432.42  Hz
F2P              0.018  ppm
F2                5.51  Hz
PPMCM          0.40415  ppm/cm
HZCM         121.34557  Hz/cm

FIG. 9A

```
Current Data Parameters
NAME              mjh-h
EXPNO                 2
PROCNO                1

F2 - Acquisition Parameters
Date_            500000
Time              17.34
INSTRUM           spect
PROBHO  5 mm QNP 1H
PULPROG            zg30
TD                32768
SOLVENT          Aceton
NS                   16
DS                    2
SMH           2637.131   Hz
FIDRES        0.080479   Hz
AQ            5.2128630  sec
RG                  181
DM             189.600   usec
DE               7.93    usec
TE              300.0    K
D1         1.00000000    sec
P1              11.30    usec
DE               7.93    usec
SF01       300.2513047   MHz
NUC1               1H
PL1             -3.00    dB F2 - Processing Parameters
SI                32768
SF         300.2500091   MHz
MDW                 EM
S58                   0
LB               1.00    Hz
GB                    0
PC               1.00

1D NMR plot parameters
CX              20.00    cm
F1P              8.040   ppm
F1            2414.09    Hz
F2P              0.383   ppm
F2             115.05    Hz
PPMCM            0.38285 ppm/cm
HZCM           114.95186 Hz/cm
```

FIG. 10A

```
Current Data Parameters
NAME              mjh-h
EXPNO                 2
PROCNO                1

F2 - Acquisition Parameters
Date_            500000
Time              22.03
INSTRUM           spect
PROBHO   5 mm QNP jH
PULPROG            zg30
TD                32768
SOLVENT          Aceton
NS                   16
DS                    2
SMH            2759.382    Hz
FIDRES          0.084210   Hz
AQ              5.9376116  sec
RG                  181
DM              181.200    usec
DE                7.93     usec
TE              300.0      K
D1              1.00000000 sec
P1               11.30     usec
DE                7.93     usec
SF01          300.2512375  MHz
NUC1               1H
PL1              -3.00     dB F2 - Processing Parameters
SI                32768
SF            300.2500090  MHz
MDW                  EM
S58                   0
LB                 1.00    Hz
GB                    0
PC                 1.00

1D NMR plot parameters
CX               20.00     cm
F1P               8.048    ppm
F1             2416.54     Hz
F2P              -0.072    ppm
F2              -21.50     Hz
PPMCM           0.40600    ppm/cm
HZCM          121.90218    Hz/cm
```

COMPOUND HAVING THIOL ANCHORING GROUP, METHOD OF SYNTHESIZING THE SAME, AND MOLECULAR ELECTRONIC DEVICE HAVING MOLECULAR ACTIVE LAYER FORMED USING THE COMPOUND

The present patent application is a Divisional of application Ser. No. 11/398,188, filed Apr. 4, 2006 now U.S. Pat. No. 7,538,199.

CROSS-REFERENCE TO RELATED PATENT APPLICATION

This application claims the benefit of Korean Patent Application No. 10-2005-0089516, filed on Sep. 26, 2005, in the Korean Intellectual Property Office, the disclosure of which is incorporated herein in its entirety by reference.

BACKGROUND OF THE INVENTION

1. Field of the Invention

The present invention relates to a compound having a functional group which provides electrical characteristics, a method of synthesizing the compound, and a molecular electronic device formed using the compound, and more particularly, to a compound having an azo compound in which an electron acceptor and electron donor are coupled, a method of synthesizing the compound, and a molecular electronic device having a molecular active layer formed using the compound.

2. Description of the Related Art

Conventional molecular electronic devices include a pair of metal electrodes and an organic molecular layer interposed therebetween. The organic molecular layer has organic semiconductor characteristics when interposed between the pair of metal electrodes.

Recently, it was discovered that an organic material has semiconductor characteristics due to conjugation bonding of π-electrons, which has sparked further interest in organic semiconductor materials. Most of the research into organic materials has been related to electron transporting. Applications of molecular electronic devices to molecular switching devices and memory devices using a charging phenomenon caused by the polarization of π-electrons have been actively researched. In particular, as commercial nano-sized semiconductor products are being developed, the development of ultra thin and fine molecular electronic devices is increasingly in demand.

SUMMARY OF THE INVENTION

The present invention provides a compound that has a new structure suitable for the realization of a nano-sized molecular electronic device.

The present invention also provides a method of synthesizing a compound that has a new structure suitable for the realization of a nano-sized molecular electronic device.

The present invention also provides an ultra thin film nano-sized molecular electronic device having a nano-sized microstructure and good memory and switching characteristics due to the inclusion of a molecular active layer in the form of a single molecular layer.

According to an aspect of the present invention, there is provided a compound for forming a molecular electronic device, including: an azo compound that comprises a dinitrothiophene group and an aminobenzene group having thiol derivatives.

The azo compound may include a disulfide group having a ring structure.

The azo compound may include the following structure:

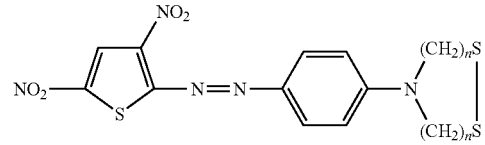

where n is an integer ranging from 1 to 20.

The azo compound may include a thioacetate group.

The azo compound may include the following structure:

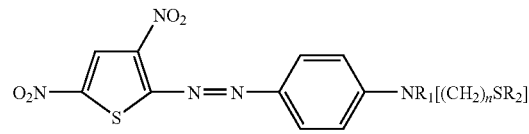

where n is an integer ranging from 1 to 20; $R_1$ is a hydrogen atom, an alkyl of $C_1$ to $C_{20}$, phenyl, or $(CH_2)_nSR_2$; and $R_2$ is a hydrogen atom, acetyl, or a methyl group.

The azo compound may include the following structure:

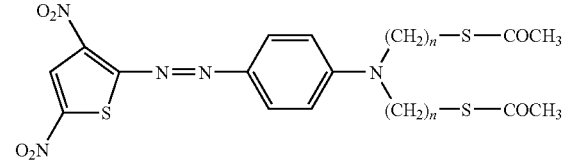

where n is an integer ranging from 1 to 20.

According to another aspect of the present invention, there is provided a method of synthesizing a compound for forming a molecular electronic device, the method including: forming an aminobenzene compound having thiol derivatives by reacting a material selected from the group consisting of aniline and aniline derivatives with sulfide; forming a diazonium intermediate compound from 2-amino-3,5-dinitrothiophene; and azo coupling the aminobenzene compound having the thiol derivatives with the diazonium intermediate compound.

The aminobenzene compound having the thiol derivatives may include one of the following structures:

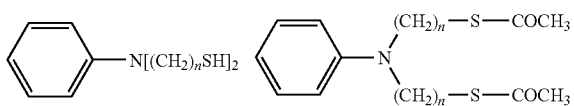

where n is an integer ranging from 1 to 20.

According to another aspect of the present invention, there is provided a molecular electronic device including: a first electrode; a second electrode formed on the first electrode; and a molecular active layer interposed between the first electrode and the second electrode, wherein the molecular active layer is formed of the compound for forming a molecular electronic device according to the present invention.

The molecular active layer may form a switching device switching between an on-state and an off-state in response to a voltage applied between the first and second electrodes.

The molecular active layer may form a memory device storing a predetermined electric signal in response to a voltage applied between the first and second electrodes.

The molecular active layer may be self-assembled on the first electrode using the thiol derivatives in the azo compound as an anchoring group.

According to an aspect of the present invention, an azo compound in which an electron acceptor and an electron donor are coupled is immobilized on a metal electrode through self-assembly, thereby forming a molecular active layer in the form of a single molecular layer. The molecular electronic device provides good memory and switching characteristics. The compound can be advantageously used for the formation of an ultra thin film nano-sized molecular electronic device.

BRIEF DESCRIPTION OF THE DRAWINGS

The above and other features and advantages of the present invention will become more apparent by describing in detail exemplary embodiments thereof with reference to the attached drawings in which:

FIG. 5 and FIG. 5A are $^1$H-nuclear magnetic resonance (NMR) spectrums of another compound illustrated in FIG. 3;

FIG. 6 and FIG. 6A are $^1$H-NMR spectrums of another compound illustrated in
FIG. 3;

FIG. 7 and FIG. 7A are $^1$H-NMR spectrums of another compound illustrated in FIG. 3;

FIG. 8 and FIG. 8A are $^1$H-NMR spectrums of another compound illustrated in FIG. 3;

FIG. 9 and FIG. 9A are $^1$H-NMR spectrums of another compound illustrated in FIG. 3;

FIG. 10 and FIG. 10A are $^1$H-NMR spectrums of another compound illustrated in FIG. 3;

DETAILED DESCRIPTION OF THE INVENTION

Figure 1:
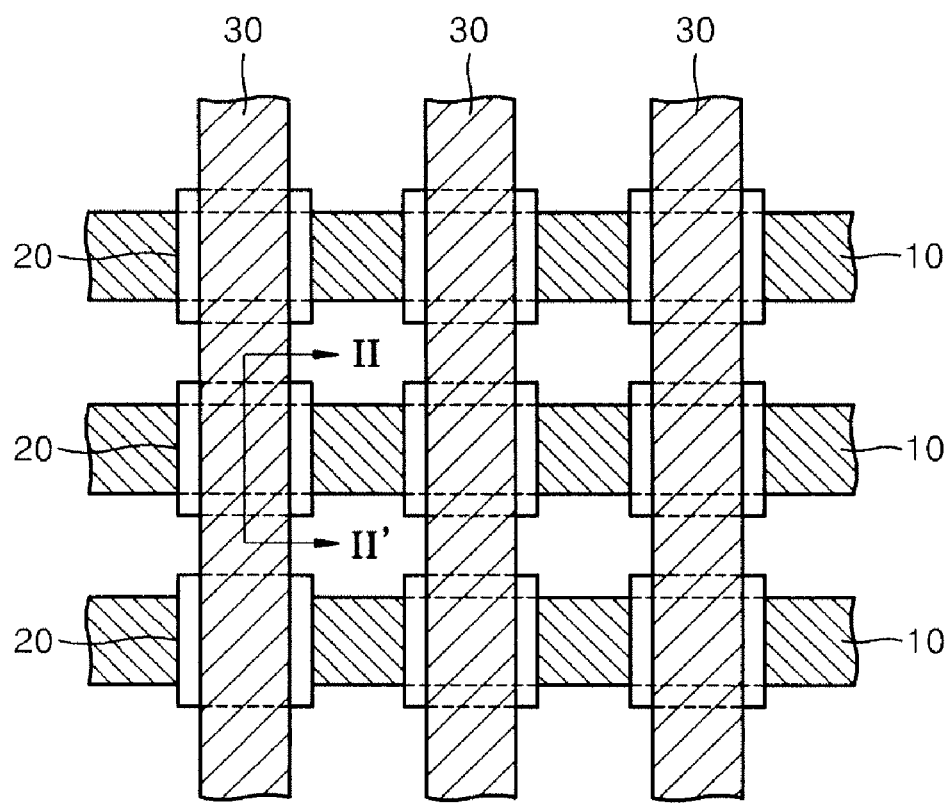
FIG. 1 is a schematic layout of a molecular electronic device according to an embodiment of the present invention.

The present invention will now be described with reference to the attached drawings in which exemplary embodiments of the present invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

The present invention provides a compound used for forming a molecular electronic device having switching and memory characteristics and a method of synthesizing the compound. According to an embodiment of the present invention, the compound used for forming a molecular electronic device comprises an azo compound having an electron acceptor-azo-electron donor-thiol structure providing switching and memory characteristics. According to an embodiment of the present invention, the compound includes a dinitrothiophene group as an electron acceptor and an aminobenzene group as an electron donor. The electron acceptor group and electron donor group are connected to each other via an azo group.

The compound used for forming a molecular electronic device according to an embodiment of the present invention includes a specific functional group (an alligator clip), for example, an alkyl thiol. The specific functional group is selectively attached to an electrode such that organic molecules arrange in a single molecular layer to form a molecular active layer having functionality through immobilization technique of self-assembly. For this purpose, a compound according to an embodiment of the present invention includes a thioacetate group as an electron donor group.

In an embodiment of the present invention, a single molecular layered thin film is formed on a lower metal electrode through self assembly of the compounds according to embodiments of the present invention, and thus a molecular electronic device having an electrode-organic thin film-electrode structure is formed, thereby providing a molecular memory device and a molecular switch device.

Azo compounds used for forming a molecular electronic device according to an embodiment of the present invention include a disulfide group having a ring structure as an electron donor. The structure of the compounds according to an embodiment of the present invention is illustrated in formula 1.

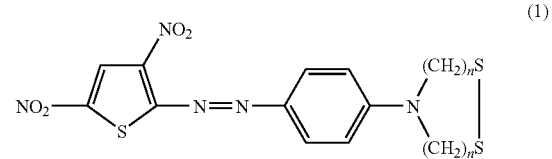

(1)

where n is an integer ranging from 1 to 20.

Azo compounds used for forming a molecular electronic device according to another embodiment of the present invention include a thioacetate group in an electron donor. The structure of the compounds according to an embodiment of the present invention is illustrated in formula 2.

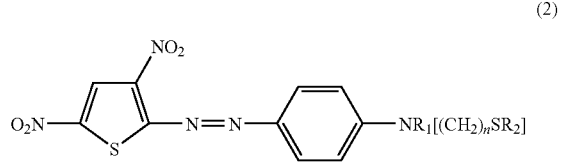

(2)

where n is an integer ranging from 1 to 20; $R_1$ is a hydrogen atom, an alkyl of $C_1$ to $C_{20}$, phenyl, or $(CH_2)_nSR_2$, wherein $R_2$ is a hydrogen atom, acetyl, or a methyl group.

The azo compounds according to an embodiment of the present invention may have a structure of formula 3 illustrated below.

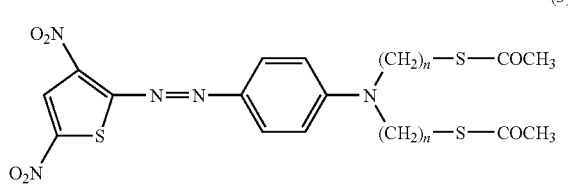

(3)

where n is an integer ranging from 1 to 20.

In order to use the above-described compound to form a molecular electronic device according to an embodiment of the present invention, a material selected from the group consisting of aniline and aniline derivatives is reacted with a sulfide to synthesize an aminobenzene compound having thiol derivatives. Formula 4 provides examples of aminobenzene compounds having thiol derivatives which can be obtained using a method of synthesizing a compound used for forming a molecular electronic device according to an embodiment of the present invention.

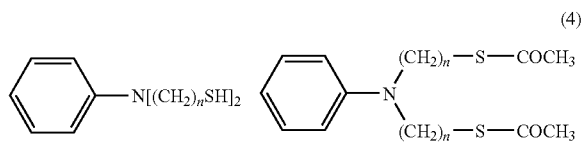

(4)

In addition, a diazonium intermediate compound is formed from 2-amino-3,5-dinitrothiophene. The diazonium intermediate compound is azo-coupled with the aminobenzene compound having the thiol derivatives of formula 4. A method of synthesizing a compound used for a molecular electronic device according to an embodiment of the present invention will be described later.

In embodiments of the present invention, the above-described compounds are immobilized on a lower electrode through self-assembly to form a single molecular layer, and an upper electrode is formed on the single molecular layer, thereby forming a molecular electronic device. That is, the molecular electronic device according to an embodiment of the present invention has a molecular active layer including at least one organic thin film interposed between a pair of electrodes. The molecular active layer is formed of an azo compound having a dinitrothiophene group as an electron acceptor and an aminobenzene group having thiol derivatives as an electron donor. For example, the molecular active layer may be a single molecular layer formed through self-assembly of the compound of formula 1 or 2 on the lower electrode.

Figure 2:
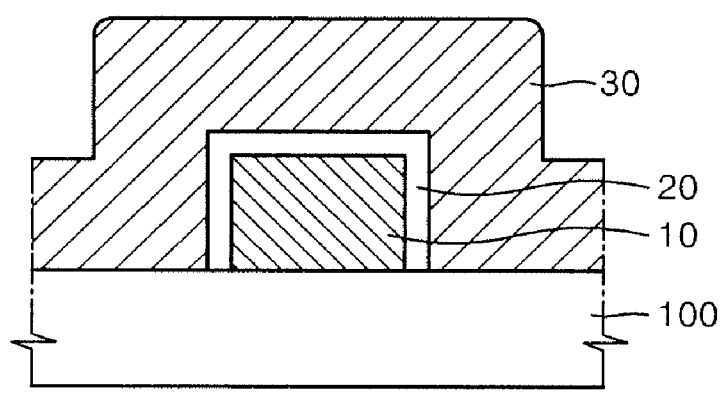
FIG. 2 is a cross-sectional view of FIG. 1 taken along line II-II'.

FIG. 1 is a schematic layout of a molecular electronic device according to an embodiment of the present invention. FIG. 1 illustrates an example of a molecular electronic device in which lower electrodes 10 and upper electrodes 30 form a 3×3 array. FIG. 2 is a cross-sectional view of FIG. 1, taken along line II-II'.

Referring to FIGS. 1 and 2, the lower electrodes 10 and the upper electrodes 30 extend perpendicularly to each other to cross each other at predetermined positions on a substrate 100. A molecule active layer 20 is interposed between the lower electrodes 10 and the upper electrodes 30. The molecular active layer 20 is formed of the compounds according to embodiments of the present invention described above. Thiol derivatives such as alkyl thiol act as a specific functional group (alligator clip) in the compounds according to embodiments of the present invention. That is, the compounds according to embodiments of the present invention employ the thiol derivatives as an anchoring group and are selectively combined with the lower electrode 10 through self-assembly, thereby forming the molecular active layer 20 on the lower electrode 10. The appropriate selection of values of n in formulas 1 through 3 can control the thickness of the molecular active layer 20.

The lower electrodes 10 and the upper electrodes 30 may be made of gold, platinum, silver, or chrome.

The molecular electronic device having the above-described structure can form a switching device that switches between an on-state and an off-state. In addition, the molecular electronic device according to the present embodiment can form a memory device storing predetermined data in response to voltages applied to the lower electrodes 10 and the upper electrodes 30.

Figure 3:
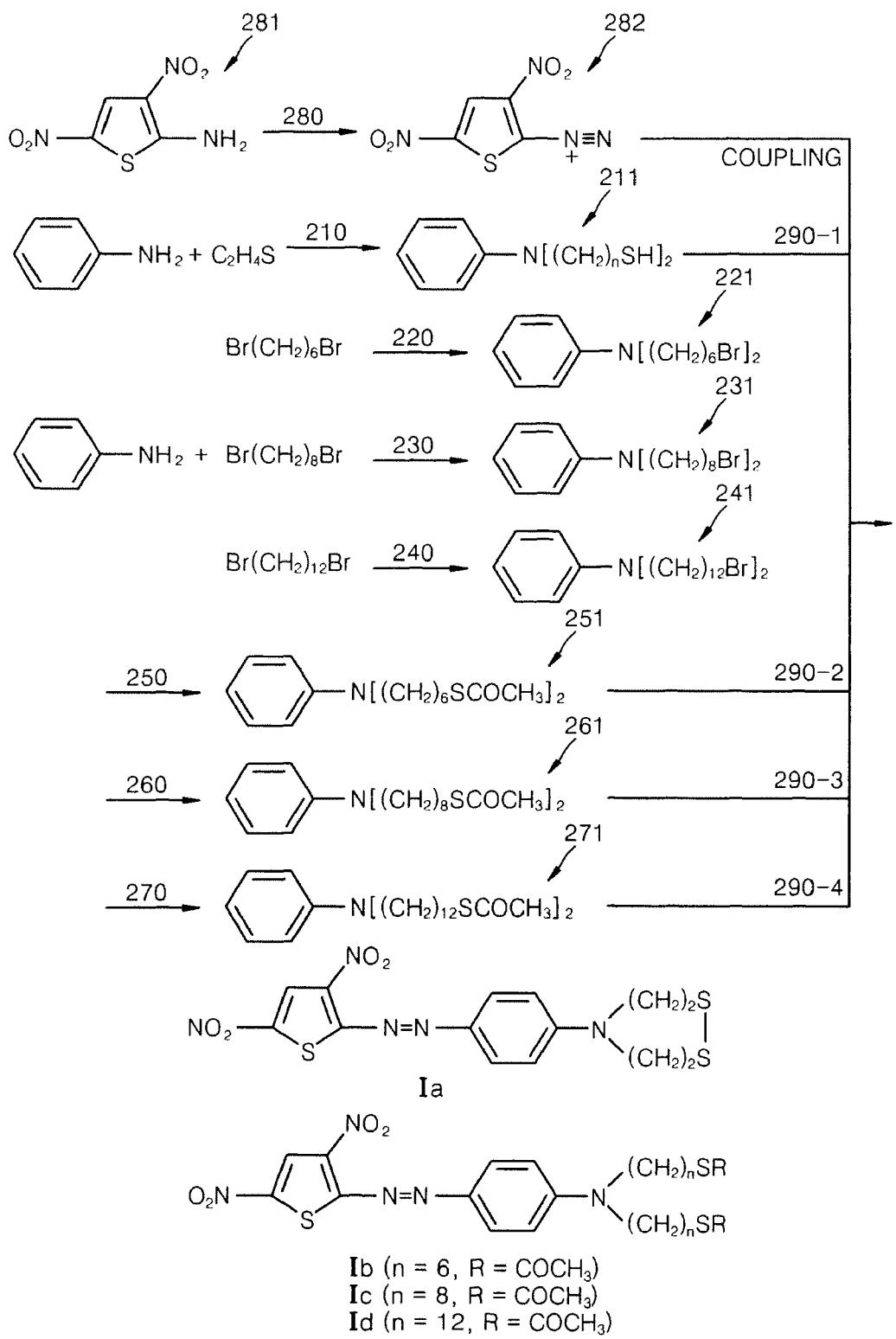
FIG. 3 is a reaction scheme for synthesizing compounds used for forming a molecular electronic device according to an embodiment of the present invention.

FIG. 3 is a reaction scheme for synthesizing compounds used for a molecular electronic device according to an embodiment of the present invention. FIG. 3 illustrates processes of synthesizing compounds which have electron donor-azo-electron acceptor structures with thiol groups.

When forming an electron donor, in order to introduce a disulfide group having a ring structure into an aminobenzene group, a dithiol compound 211 is synthesized according to synthesis process 210. In the synthesis process 210, a compound Ia, which can form a self-assembled thin film without a thioacetate protection group, is synthesized.

In order to introduce the thioacetate protection group into the electron donor, bis-(n-bromo-alkyl)-phenylamine intermediate compounds 221, 231 and 241 can be formed in synthesis processes 220, 230 and 240, respectively. The reaction times of the synthesis processes 220, 230 and 240 may be equal to or less than about 10 hours.

In order to introduce a thio group into the electron donor, new electron donor compounds 251, 261 and 271 can be formed in synthesis processes 250, 260 and 270, respectively. The reaction times of the synthesis processes 250, 260 and 270 may be equal to or less than about 1 hour. All of the compounds obtained in these processes can be confirmed as the target compounds in the reaction scheme of FIG. 3 using $^1$H/$^{12}$C-nuclear magnetic resonance (NMR) spectra and mass spectrograph spectra. Detailed experimental results will be described later.

In synthesis process 280, a diazonium intermediate compound 282 can be formed in order to perform azo coupling between the electron acceptor group and the electron donor group. The reaction conditions can be appropriately set according to the length of an alkyl chain included in a target product. In an embodiment of the present invention, a well-known method in which liquid acid and sodium nitrite are used is employed to synthesize the diazonium intermediate compound 282 which will be used to synthesize the compound Ia, and compounds Ib and Ic. A dithiol having no protection group (the compound 211 in FIG. 3) is reacted in an acid condition to synthesize the compound Ia having a disulfide ring structure.

To synthesize a compound Id, liquid acid, nitrosyl sulfuric acid, and ethanol, in which the compound 271 is easily dissolved, are added to increase reaction yield. Practically, when alkyl chains in a compound are long, an organic solvent should be used instead of a water-soluble solvent. An organic solvent that can be mixed with a water-soluble solvent may be used. In addition, if the temperature is maintained under 5° C.

during the entire reaction, the product yield can increase. The reaction time may be about 2 to 4 hours. The obtained compounds Ia, Ib, Ic, and Id can be confirmed as the target compounds using $^1$H/$^{13}$C-NMR spectra and mass spectrograph spectra. Detailed experimental results will be described later.

In order to manufacture a molecular electronic device according to an embodiment of the present invention, three lines of lower electrodes are formed using a conventional compound semiconductor process. The lower electrodes are formed using, for example, a nano-imprint process. Self assembly is an immobilization technique for forming molecular layers made of compounds according to embodiments of the present invention on the surfaces of the lower electrodes. For this, a substrate on which the lower electrodes are formed can be dipped into a solution in which the compound according to an embodiment of the present invention is dissolved. In an embodiment of the present invention, a solvent suitable for dissolving the compound may be anhydrous and oxygen-free dimethylformamide (DMF). In an embodiment of the present invention, a product having lower electrodes is dipped for about 24 hours in a solution obtained by dissolving 1 mmol of the compound according to an embodiment of the present invention in a DMF solvent, and thus single molecular layers are formed on the surfaces of the lower electrodes through self-assembly. The product in which the single molecular layers are formed on the lower electrodes is cleaned and dried in a vacuum, and then upper electrodes are deposited on the single molecular layers.

The molecular electronic device according to an embodiment of the present invention can be tested using a semiconductor parameter analyzer (HP 4156C) to confirm the switching characteristics thereof. In addition, the molecular electronic device can be tested using a pulse generator unit (HP 41501 expander) and a SMU-PGU selector (HP 16440A) to confirm memory characteristics thereof. Detailed experimental results will be described later.

The present invention will now be described in greater detail with reference to the following examples. The following examples are for illustrative purposes only and are not intended to limit the scope of the invention.

EXAMPLE 1

Synthesis of Dithiol Compound (Synthesis Process 210 in FIG. 3)

Figure 4:
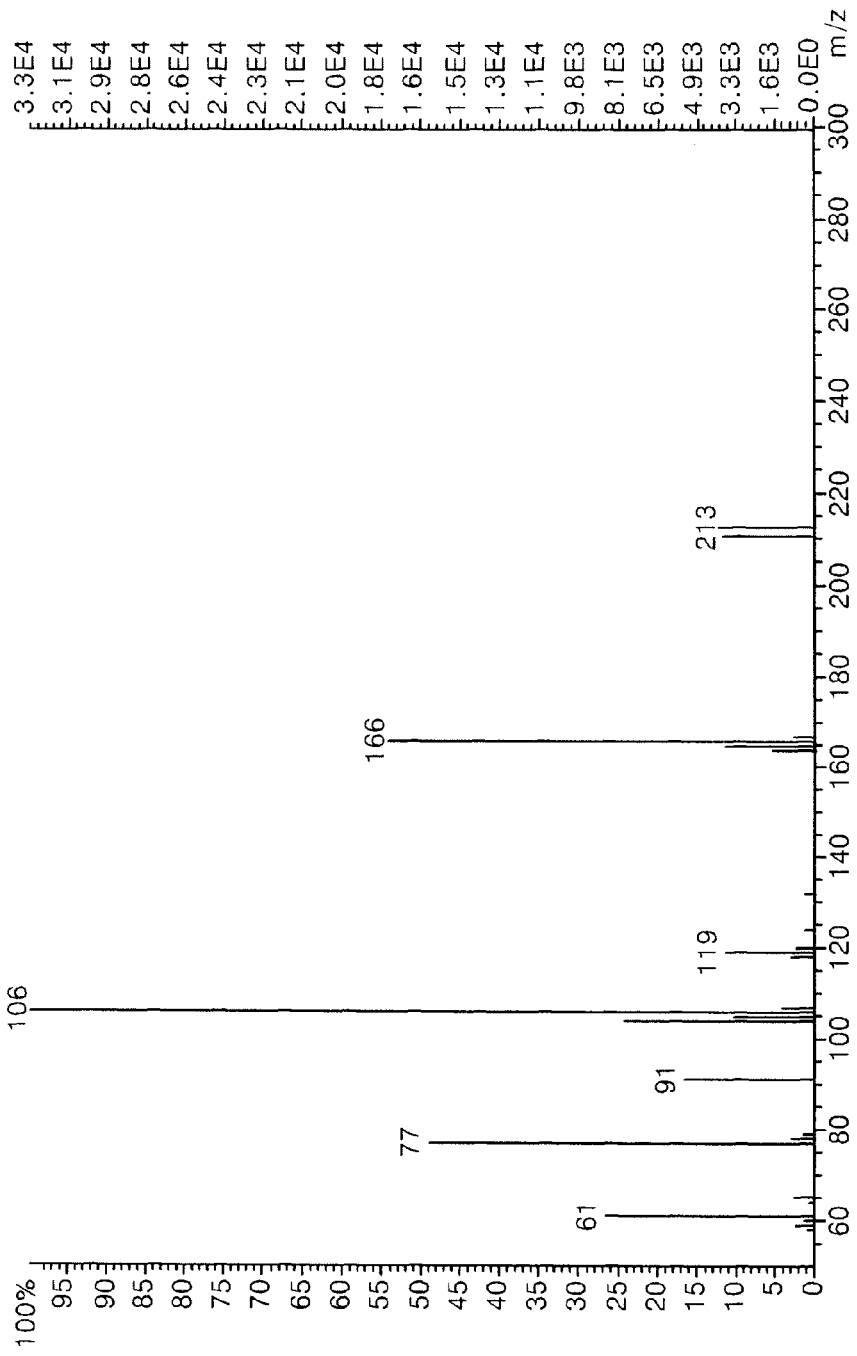
FIG. 4 is the mass spectrum of a compound illustrated in FIG. 3.

A glass autoclave was dried in an oven to maintain the anhydrous property of the glass autoclave, and then the glass autoclave was cooled. 1.03 ml of aniline (10.74 mmol) and 1.55 ml of ethylene sulfide ($C_2H_4S$) (25.78 mmol) were charged in the glass autoclave, heated to about 90 to 100° C., and maintained at this temperature for about 36 hours. The obtained product was cooled down in air. Some of the product was treated to extract organic layers using a methylene chloride solvent, the solvent was removed through reduced pressure distillation, and then the compound 211 of FIG. 3 was obtained using a silica-gel thin layer chromatography (TLC). The compound 211 was confirmed through mass spectrometry. The results are shown in FIG. 4.

Mass: m/z(M$^+$): 213

EXAMPLE 2

Synthesis of Bis-(6-bromo-hexyl)-phenyl-amine (Synthesis Process 220 in FIG. 3)

Figure 5:
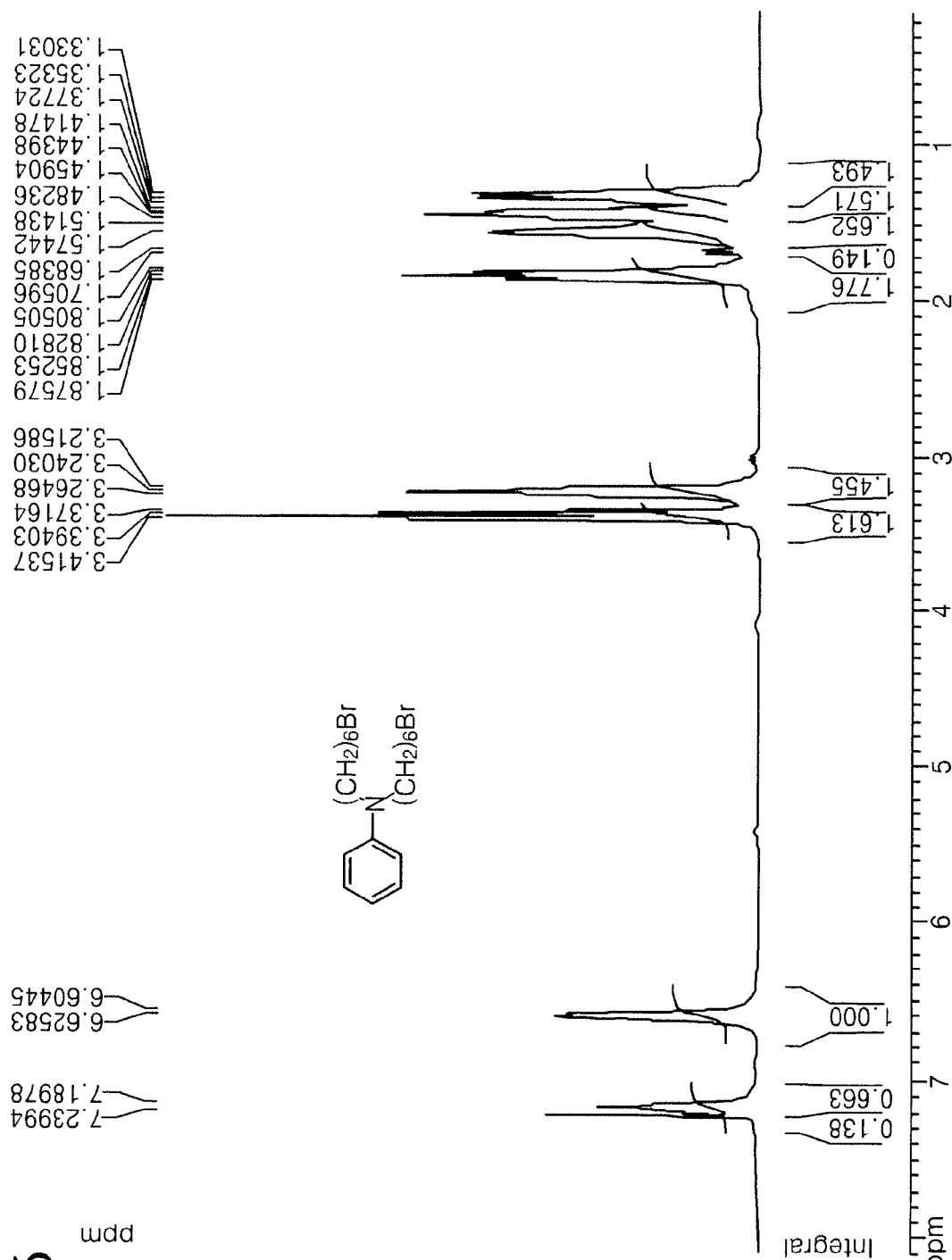

0.45 ml of aniline (5 mmol), 2.5 ml of dibromohexane (14.6 mmol), and sodium acetate (14.5 mmol) were charged in a reaction container and slowly heated to about 95 to 100° C. while generating bubbles under a nitrogen atmosphere. The reactant mixture was agitated for about 10 hours at about 95 to 100° C. The mixture was cooled down to room temperature, mixed with 30 ml of distilled water, and agitated for 10 minutes. The mixture was then treated to extract organic layers using ethylacetate, and then was distillated through reduced pressure distillation, thereby obtaining a sticky liquid. The sticky liquid was separated using preparative TLC (eluent: $CH_2Cl_2$:Hexane=1:2.5). The obtained compound was confirmed to be the compounds 221 of FIG. 3 using a $^1$H-NMR spectometry and mass spectometry. The results are shown in FIG. 5.

$^1$H NMR (300 MHz, CD$_3$Cl) δ ppm; 1.33-1.37 (4H, m), 1.41-1.48 (4H, m), 1.51-1.57 (4H, m), 1.80-1.87 (4H, m), 3.24 (4H, t), 3.39 (4H, t), 6.61 (3H, m), 7.21 (2H, m), Mass: m/z(M$^+$): 419

EXAMPLE 3

Synthesis of Bis-(8-bromo-octyl)-phenyl-amine (Synthesis Process 230 in FIG. 3)

Figure 6:
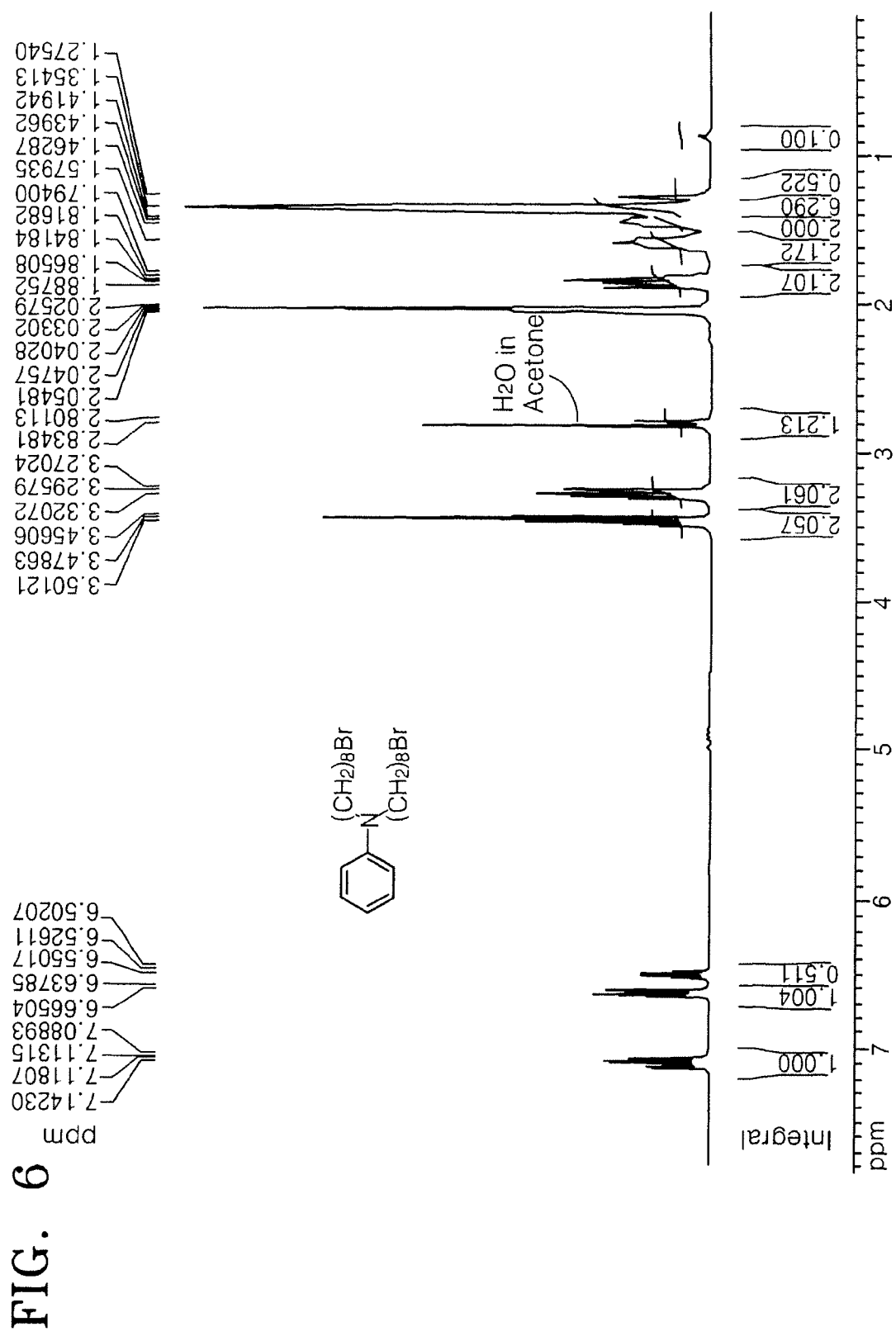

The compound 231 of FIG. 3 was synthesized using the same method as in Example 2 except that 2.7 ml of dibromooctan (14.6 mmol) was used and the agitation time for the mixture was 2.5 hours. The obtained compound was confirmed to be the compound 231 of FIG. 3 using $^1$H-NMR spectrometry and mass spectrometry. The results are shown in FIG. 6.

$^1$H NMR (300 MHz, Acetone-d$_6$) δ ppm; 1.35 (12H, m), 1.42-1.46 (4H, m), 1.58 (4H, m), 1.84 (4H, quintet), 3.29 (4H, t), 3.48 (4H, t), 6.52 (1 H, t), 6.65 (2H, d), 7.11 (2H, dd); Mass: m/z(M$^+$): 475

EXAMPLE 4

Synthesis of Bis-(12-bromo-dodecyl)-phenyl-amine (Synthesis Process 240 in FIG. 3)

Figure 7:
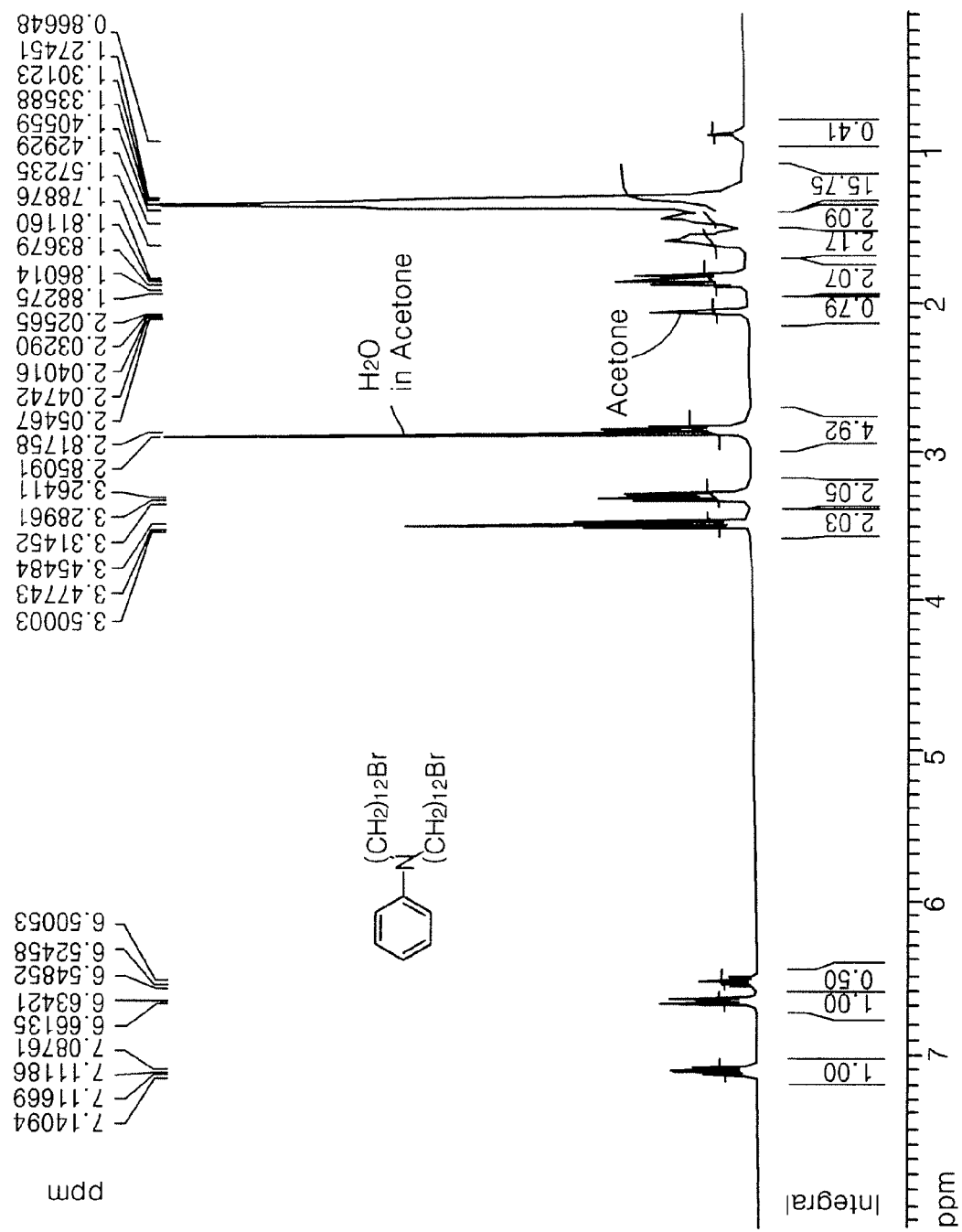

The compound 241 of FIG. 3 was synthesized using the same method as in Example 2 except that 4.8 ml of dibromododecane (14.6 mmol) was used and the agitation time for the mixture was 3.5 hours. The obtained compound was confirmed to be the compound 241 of FIG. 3 using $^1$H-NMR spectrometry and mass spectrometry. The results are shown in FIG. 7.

$^1$H NMR (300 MHz, Acetone-d$_6$) δ ppm; 1.27-1.33 (28H, m), 1.40-1.43 (4H, m), 1.57 (4H, m), 1.84 (4H, quintet), 3.29 (4H, t), 3.48 (4H, t), 6.52 (1H, t), 6.65 (2H, d), 7.11 (2H, dd); Mass: m/z(M$^+$): 587

EXAMPLE 5

Synthesis of an Aminobenzene Compound Having Thiol Derivatives (Synthesis Process 250 in FIG. 3)

Figure 8:
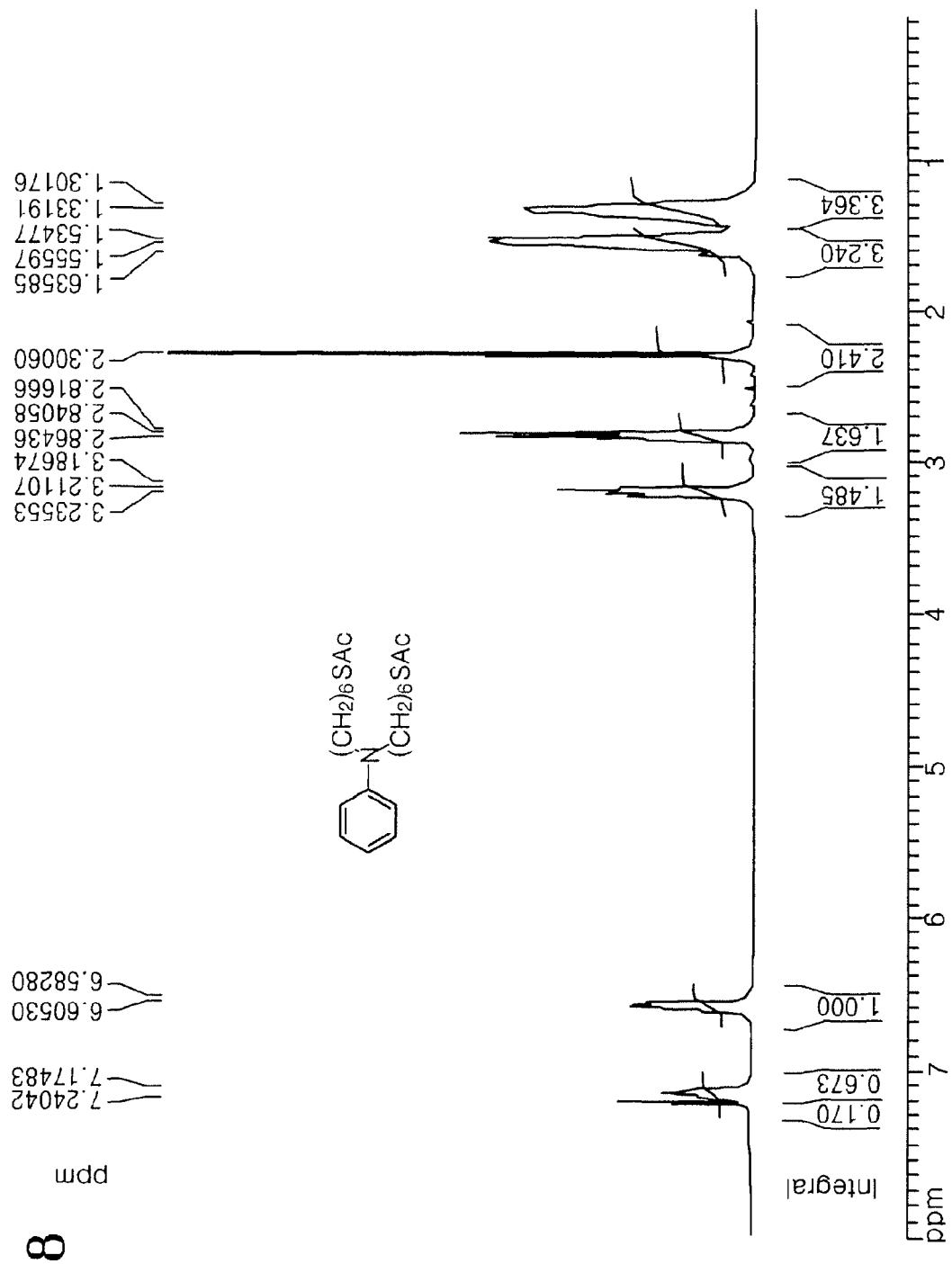

0.63 g of bis-(6-bromo-hexyl)-phenyl-amine (1.5 mmol), that is, the compound 221 of FIG. 3, obtained in Example 2, 0.51 g of potassium thioacetate (4.5 mmol), and 5 ml of N,N-dimethylacetamide (DMAc) were charged in a reaction container, and agitated for 1 hour at room temperature while generating bubbles under a nitrogen atmosphere. The mixture was mixed with 30 ml of distilled water, agitated for 10 minutes, treated to extract organic layers using ethylacetate, and distillated through reduced pressure distillation, thereby obtaining a sticky liquid. The sticky liquid was separated using preparative TLC (eluent: $CH_2Cl_2$:Hexane=1:1). The yield of the product was 79.4%. The obtained compound was confirmed to be the compound 251 of FIG. 3 using $^1$H-NMR spectrometry and mass spectrographs. The results are shown in FIG. 8.

$^1$H NMR (300 MHz, $CD_3Cl$) δ ppm; 1.30-1.33 (8H, m), 1.53-1.63 (8H, m), 2.30 (6H, s), 2.84 (4H, t), 3.21 (4H, t), 6.59 (3H, m), 7.21 (2H, m); Mass: m/z($M^+$): 409

EXAMPLE 6

Synthesis of an Aminobenzene Compound Having Thiol Derivatives (Synthesis Process 260 in FIG. 3)

Figure 9:
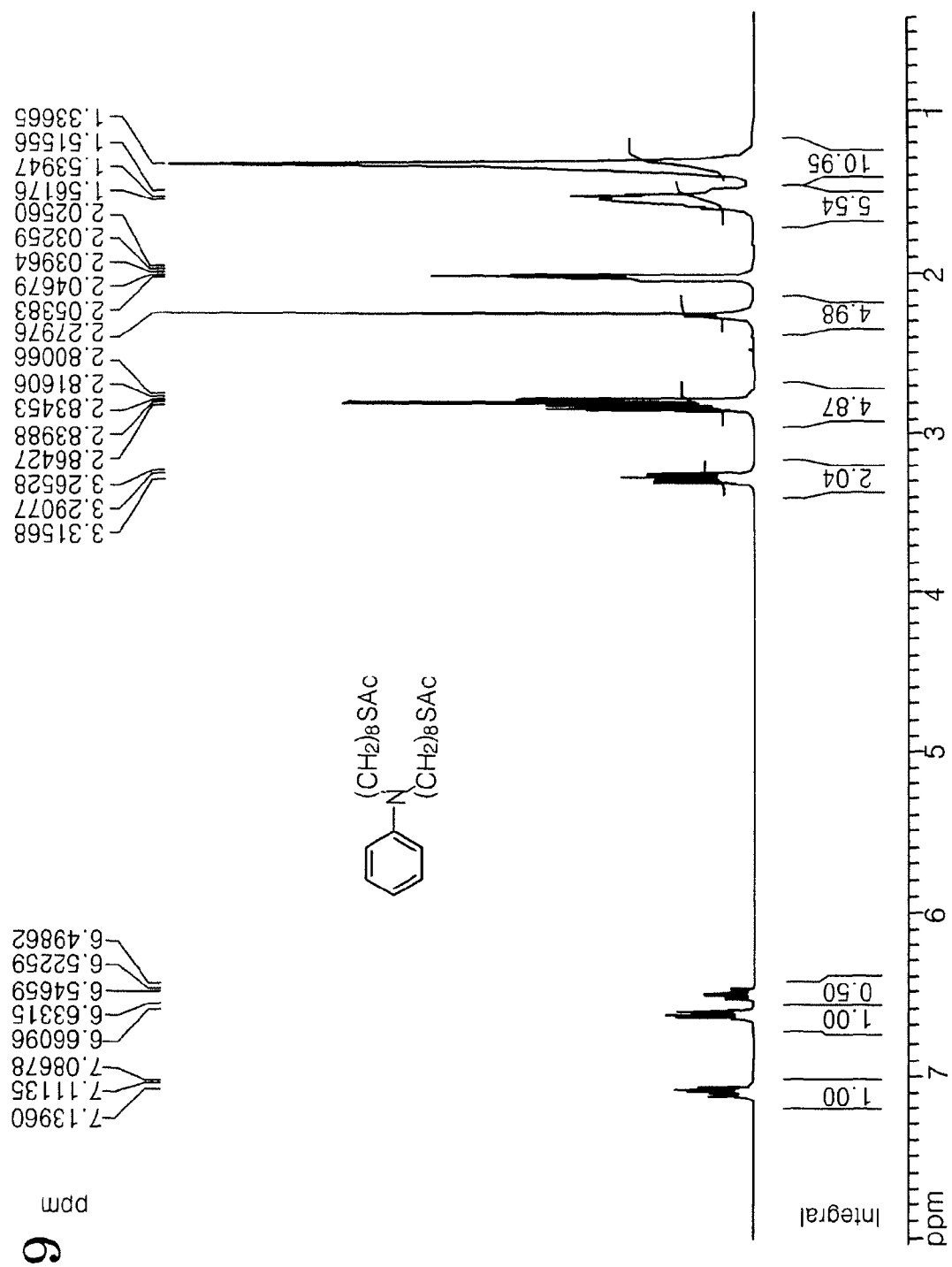

The compound 261 of FIG. 3 was synthesized using the same method as in Example 5 except that 0.71 g of bis-(8-bromo-octyl)-phenyl-amine (1.5 mmol), that is, the compound 231 of FIG. 3 obtained in Example 3, was used. The yield of the product was 69.3%. The obtained compound was confirmed to be the compound 261 of FIG. 3 using $^1$H-NMR spectrometry and mass spectrometry. The results are shown in FIG. 9.

$^1$H NMR (300 MHz, Acetone-$d_6$) δ ppm; 1.34 (18H, m), 1.51-1.56 (10H, m), 2.28 (6H, s), 2.84 (4H, t), 3.29 (4H, t), 6.52 (1H, t), 6.65 (2H, d), 7.11 (2H, dd); Mass: m/z($M^+$): 465

EXAMPLE 7

Synthesis of an Aminobenzene Compound Having Thiol Derivatives (Synthesis Process 270 in FIG. 3)

Figure 10:
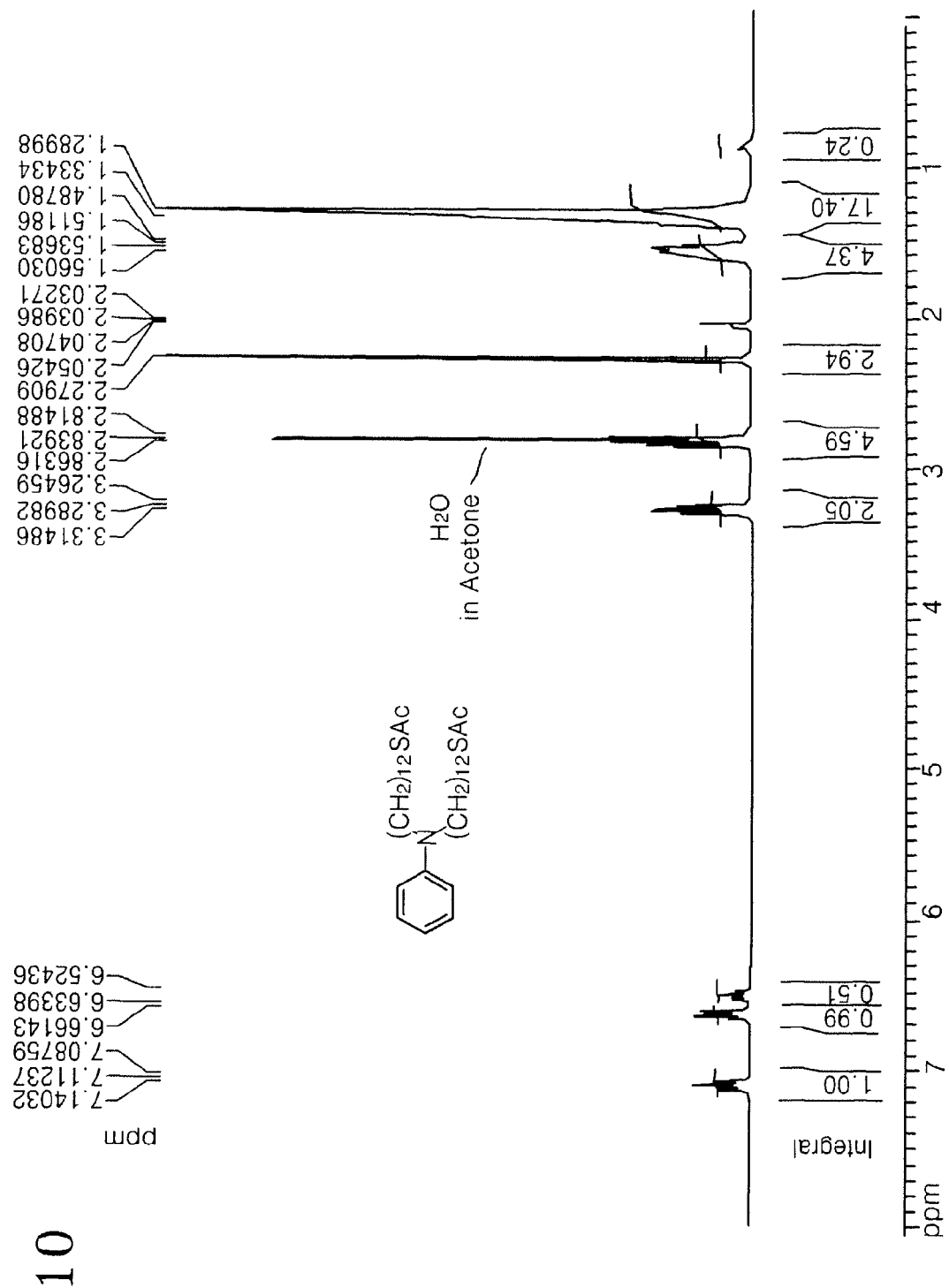

The compound 271 of FIG. 3 was synthesized using the same method as in Example 5 except that 0.88 g of bis-(12-bromo-dodecyl)-phenyl-amine (1.5 mmol), that is, the compound 241 of FIG. 3 obtained in Example 4, was used. The yield of the product was 82%. The obtained compound was confirmed to be the compound 271 of FIG. 3 using $^1$H-NMR spectrometry and mass spectrometry. The results are shown in FIG. 10.

$^1$H NMR (300 MHz, Acetone-$d_6$) δ ppm; 1.29-1.33 (32H, m), 1.51-1.56 (8H, m), 2.28 (6H, s), 2.84 (4H, t), 3.29 (4H, t), 6.52 (1H, t), 6.65 (2H, d), 7.11 (2H, dd); Mass: m/z($M^+$): 577.

EXAMPLE 8

Synthesis of an Azo Compound Having Thiol Derivatives (Synthesis Process 290-1 in FIG. 3)

0.76 g of sodium nitrite ($NaNO_2$) (11.01 mmol) was dissolved in 9.0 g of sulfuric acid. At this time, an exothermic reaction to 30° C. occurred. The mixture was agitated until returning to the room temperature, and then cooled to 5° C. Next, an acidic mixture (5 g of propionic acid+30 g of acetic acid) was slowly added to the cooled mixture. The mixture was agitated for 30 minutes at 15° C., thereby obtaining the compound 282 of FIG. 3.

Figure 11:
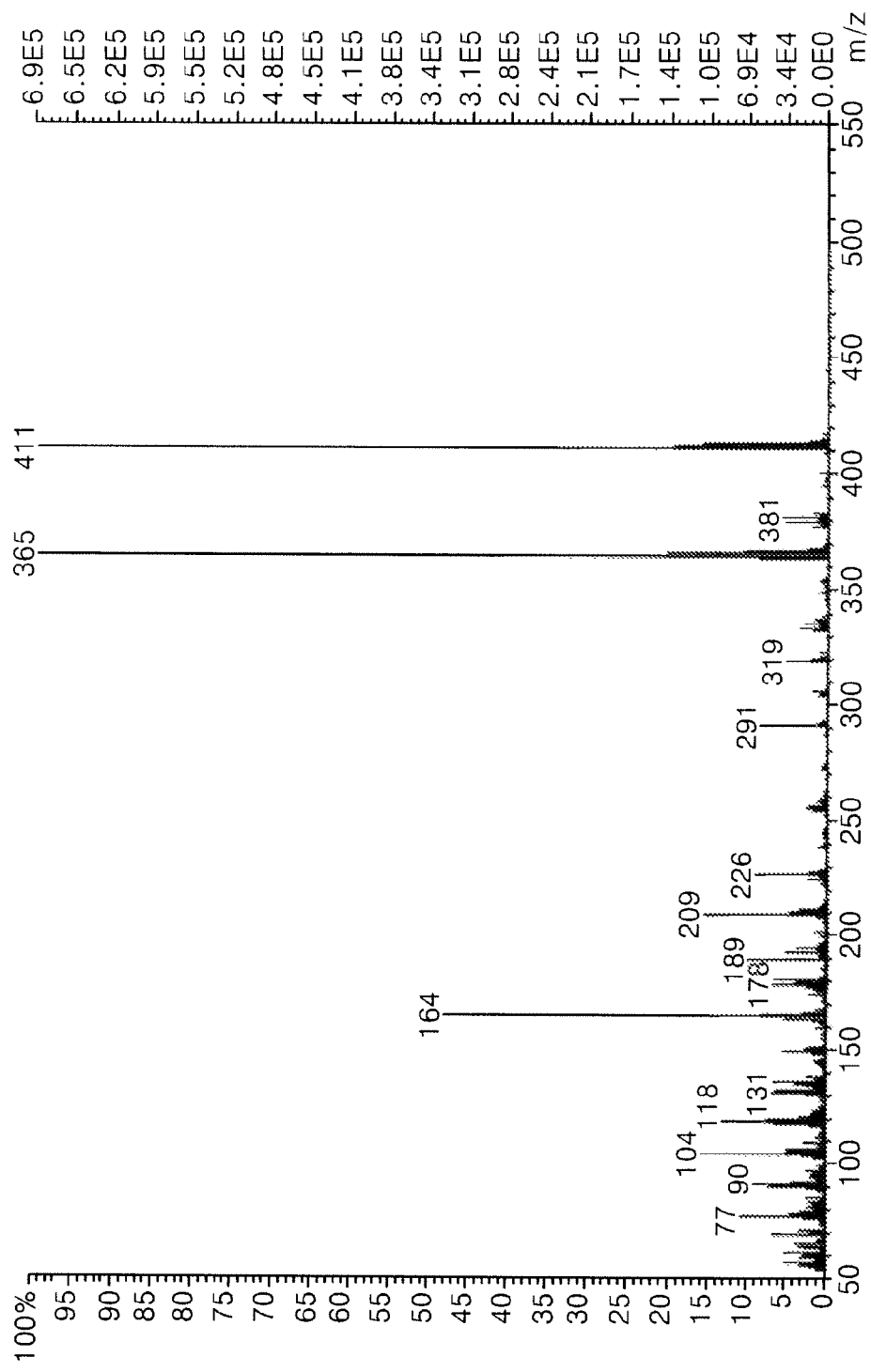
FIG. 11 is a mass spectrograph spectrum of another compound illustrated in FIG. 3.

The compound 282 was cooled to 0° C., and 1.89 g of 2-amino-3,5-dinitrothiophene (10.0 mmol) was slowly added thereto over the course of 30 minutes. The mixture was slowly added at 0° C. to a solution containing 1.53 g of the compound 211 (10.0 mmol) of FIG. 3 obtained in Example 1 and a hydrochloric aqueous solution (3.0 ml of concentrated HCl+30 ml of $H_2O$+35 g of ice). The mixture was agitated for 50 minutes at 0° C. and then filtered using a sintered funnel. The filtrates were dissolved in 200 ml of $CH_2Cl_2$, and cleaned three times with 200 ml of brine using a separatory funnel. The small amount of water was removed from the mixture using $MgSO_4$. The mixture was saturated using a rotary evaporator and the products were separated using column chromatography (eluent: EA:Hx=1:10), thereby obtaining the compound Ia of FIG. 3. The compound Ia was confirmed using $^1$H-NMR spectrometry and mass spectrometry. The results are shown in FIG. 11.

$^1$H NMR (400 MHz, $CDCl_3$) δ ppm ; 2.31 (s, 6H), 3.10 (t, 4H, J=5.6 Hz), 4.22 (t, 4H, J=5.6 Hz), 6.77 (d, 2H, J=9.3 Hz), 7.97 (d, 2H, J=9.3 Hz), 8.35 (s, 1H); Mass: m/z ($M^+$-2H): 411

EXAMPLE 9

Synthesis of an Azo Compound Having Thiol Derivatives (Synthesis Process 290-2 in FIG. 3)

0.09 g of sodium nitrite ($NaNO_2$) (1.34 mmol) was dissolved in 1.5 g of sulfuric acid. At this time, an exothermic reaction to 30° C. occurred. The mixture was agitated until returning to room temperature, and then cooled to 5° C. Next, an acidic mixture (0.4 g of propionic acid+4 g of acetic acid) was slowly added to the cooled mixture. The mixture was agitated for 30 minutes at 15° C., thereby obtaining the compound 282 of FIG. 3.

Figure 12:
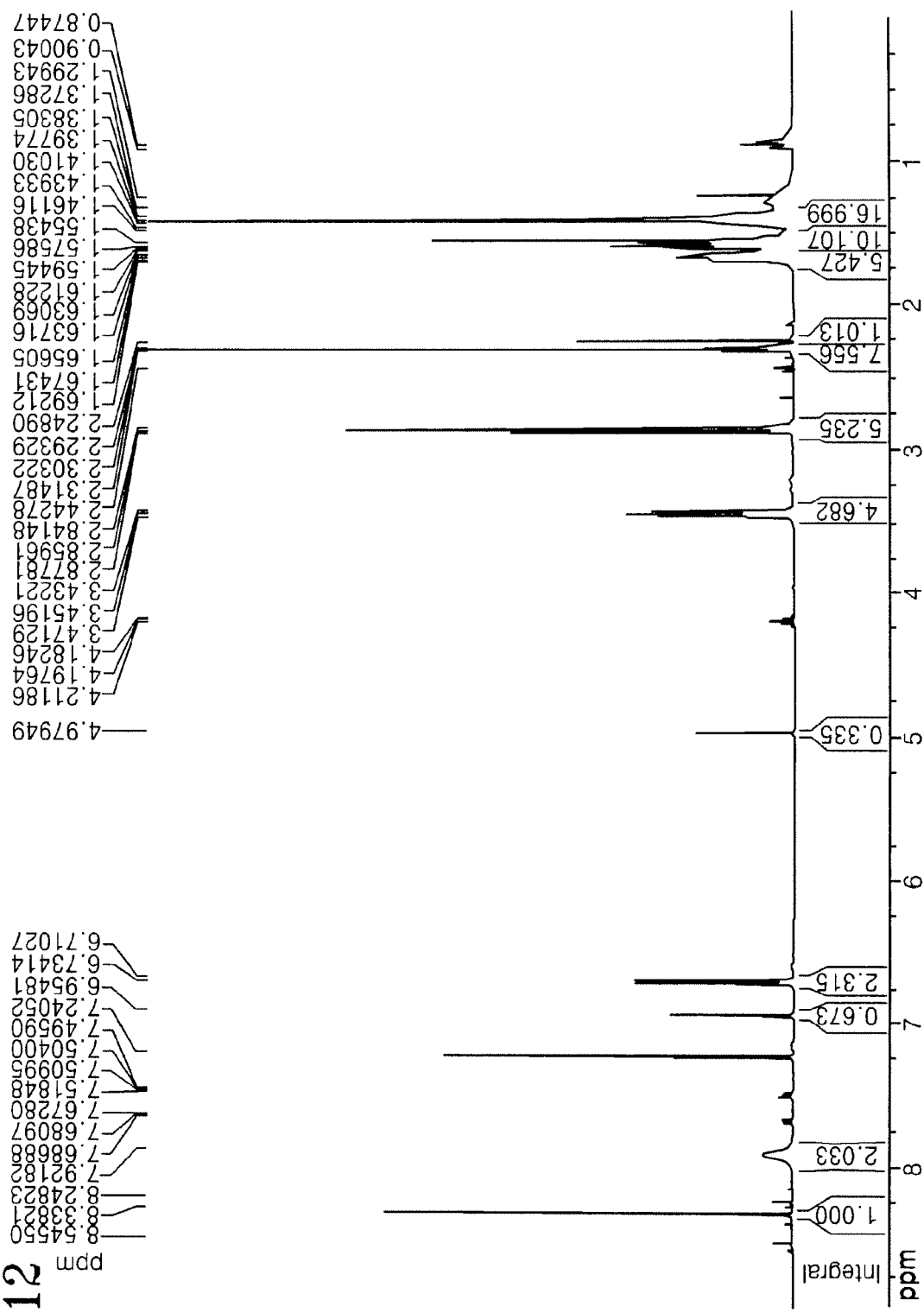
FIG. 12 is a $^1$H-NMR spectrum of another compound illustrated in FIG. 3.

The compound 282 was cooled to 0° C., and 0.23 g of 2-amino-3,5-dinitrothiophene (1.22 mmol) was slowly added thereto over the course of 30 minutes. The resulting mixture was slowly added at 0° C. to a solution containing 0.5 g of thioacetatehexyl aniline (1.22 mmol), that is, the compound 251 of FIG. 3 obtained in Example 5, and a hydrochloric aqueous solution (0.4 ml of concentrated HCl+4 ml of $H_2O$+5 g of ice). The mixture was agitated for 50 minutes at 0° C. and then filtered using a sintered funnel. The precipitated salts were dissolved in 200 ml of $CH_2Cl_2$, and cleaned three times with 200 ml of brine using a separatory funnel. The small amount of water was removed from the mixture using $MgSO_4$. The mixture was saturated using a rotary evaporator and the products were separated using column chromatography (eluent: EA:Hx=1:10), thereby obtaining the compound Ib of FIG. 3. The compound Ib was confirmed using $^1$H-NMR spectrometry and mass spectrometry. The results are shown in FIG. 12.

$^1$H NMR (400 MHz, $CDCl_3$) δ ppm; 1.23-1.69 (m, 16H), 2.31 (s, 6H), 2.86 (t, 4H, J=7.6 Hz), 3.45 (t, 4H, J=7.6 Hz), 6.72 (d, 2H, J=9.6 Hz), 7.89 (br s, 2H), 8.36 (s, 1H); Mass: m/z($M^+$): 609

EXAMPLE 10

Synthesis of an Azo Compound Having Thiol Derivatives (Synthesis Process 290-3 in FIG. 3)

0.16 g of sodium nitrite ($NaNO_2$) (1.34 mmol) was dissolved in 3 g of sulfuric acid. At this time, an exothermic reaction 30° C. occurred. The mixture was agitated until returning to room temperature, and then cooled to 5° C. Next, an acidic mixture (1.2 g of propionic acid+8 g of acetic acid) was slowly added to the cooled mixture. The mixture was agitated for 30 minutes at 15° C., thereby obtaining the compound 282 of FIG. 3.

Figure 13:
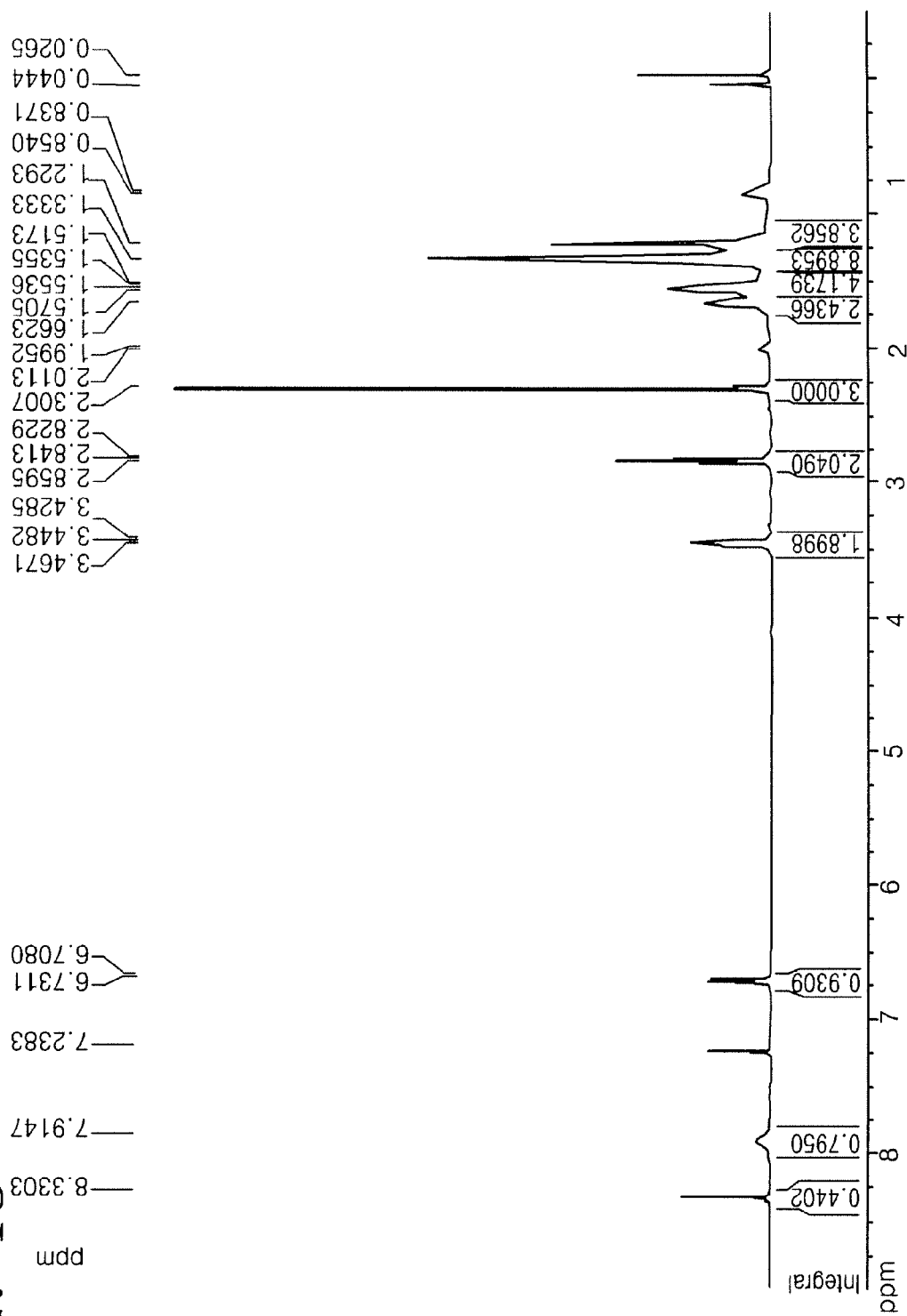
FIG. 13 is a $^1$H-NMR spectrum of another compound illustrated in of FIG. 3.

The compound 282 was cooled to 0° C., and 0.37 g of 2-amino-3,5-dinitrothiophene (198 mmol) was slowly added thereto over the course of 30 minutes. The mixture was slowly added at 0° C. to a solution containing 0.92 g of thioacetateoctyl aniline, that is, the compound 261 (1.98 mmol) of FIG. 3 obtained in Example 6, and a hydrochloric aqueous solution (0.8 ml of concentrated HCl+8 ml of $H_2O$+7 g of ice). The mixture was agitated for 80 minutes at 0° C. and then filtered using a sintered funnel. The precipitated salts were dissolved in 200 ml of $CH_2Cl_2$, and cleaned three times with 200 ml of brine using a separatory funnel. The small amount of water was removed from the mixture using $MgSO_4$. The mixture was saturated using a rotary evaporator and the products were separated using column chromatography (eluent: EA:Hx=1: 10), thereby obtaining the compound Ic of FIG. 3. The compound Ic was confirmed using $^1$H-NMR spectrometry and mass spectrometry. The results are shown in FIG. 13.

$^1$H NMR (400 MHz, $CDCl_3$) δ ppm; 1.23-1.67 (m, 20H), 2.30 (s, 6H), 2.84 (t, 8H, J=7.7 Hz), 3.45 (t, 4H, J=7.7 Hz), 6.72 (d, 2H, J=9.3 Hz), 7.92 (br s, 2H), 8.35 (s, 1H); Mass: m/z($M^+$) : 665

EXAMPLE 11

Synthesis of an Azo Compound Having Thiol Derivatives IV (Synthesis Process 290-4 in FIG. 3)

Figure 14:
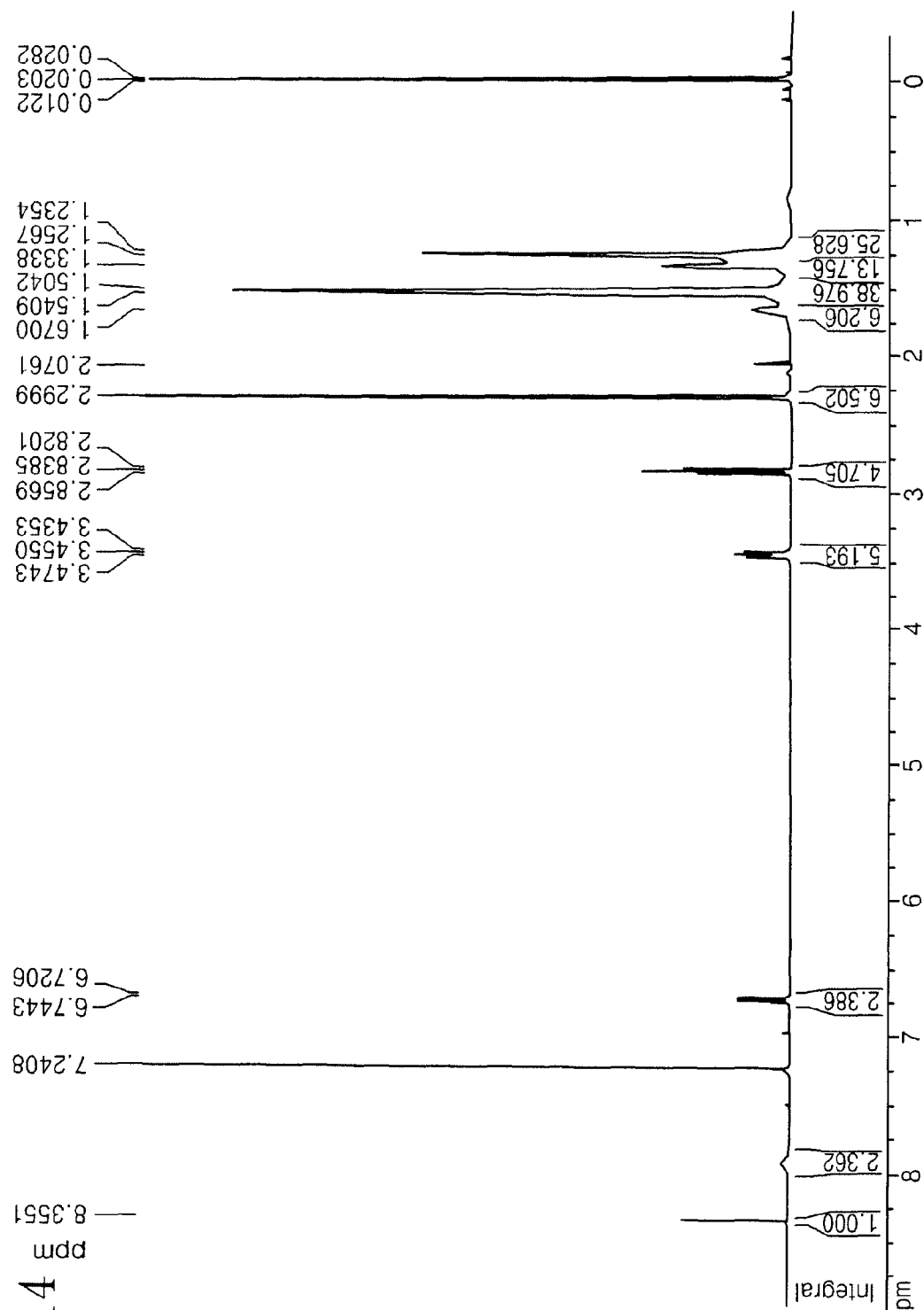
FIG. 14 is a $^1$H-NMR spectrum of another compound illustrated in FIG. 3.

The reaction conditions in the present example were different from those in Examples 9 and 10 because the compound 241 of FIG. 3 is insoluble. 1.9 g of 2-amino-3,5-dinitrothiophene (0.01 mol) was dispersed in 12 ml of an acidic mixture (acetic acid : propionic acid=6:1 (VN)) and agitated for 10 minutes below 10° C. 2.2 ml of 40% nitrosylsulfuric acid ($NOHSO_4$) (0.011 mol) was slowly added to the solution over the course of 30 minutes while maintaining the temperature below 5° C., and the result was agitated for 1 hour at 5° C. In order to remove excessive sodium nitrite ($NaNO_2$), a small amount of urea (0.1 g) was added and the mixture was agitated for 20 minutes at 5° C. This solution was slowly added for 30 minutes to another solution containing 5.77 g of thioacetatedodecyl aniline (0.01 mol) and acetic acid/EtOH (V/V=1/1) while maintaining the temperature below 5° C. Here, sodium acetate was used to maintain the pH of the resultant reactant in a range from 2.0 to 2.5. The reactant was added to 150 ml of ice cold $H_2O$, agitated for 30 minutes, and then filtered using a sintered funnel. The precipitated salts were dispersed in 30 ml of a 10% $NaHCO_3$ solution, agitated for 10 minutes, filtered, and cleaned using a small amount of isopropanol. Next, the products were separated using column chromatography (eluent: $CH_2Cl_2$: Hx=2: 1), thereby obtaining the compound Id of FIG. 3. The compound Id was confirmed using $^1$H-NMR spectrometry and mass spectrometry. The results are shown in FIG. 14.

$^1$H NMR (400 MHz, $CDCl_3$) δ ppm; 1.23-1.67 (m, 40H), 2.29 (s, 6H), 2.83 (t, 4H, J=7.7 Hz), 3.45 (t, 4H, J=7.7 Hz), 6.73 (d, 2H, J=9.5 Hz), 7.93 (br s, 2H), 8.36 (s, 1H); Mass: m/z($M^+$): 777

EXAMPLE 12

Manufacture of a Molecular Electronic Device Having Switching and Memory Characteristics To immobilize the compounds 1a, 1b, 1c, and 1d respectively obtained in Examples 8 through 11 on electrodes of a molecular electronic device, self-assembly was employed. First, lower electrodes were formed using gold. The lower electrodes were arranged in a three-line pattern using a conventional compound semiconductor process. The lower electrodes were formed using a nano-imprint process. Conventionally, the line width of the lower electrodes is appropriately 5 to 50 μm. In the present example, the lower electrodes were formed to a line width of 5 μm and a thickness of 50 μm.

The compounds Ia, Ib, Ic and Id were dissolved in chloroform, dichloromethane, THF, or a DMF solvent. In the present example, 10 ml solutions respectively containing 1 mmol of the compounds Ia, Ib, Ic, and Id dissolved in a DMF solvent were prepared. For this process, an oxygen-free, anhydrous DMF solvent could have been used in a glove box in an oxygen-free, anhydrous environment.

The products having the lower electrodes were respectively dipped in the prepared solutions, and thus molecular layers of the compounds Ia, Ib, Ic and Id were respectively immobilized on the surfaces of the lower electrodes through self-assembly. After being dipped for about 24 hours, each of the products, in which the molecular layer was formed on the surfaces of the lower electrodes, was cleaned sequentially using DMF, THF, ethanol, and distilled water. Each of the cleaned products was dried for more than 2 hours in a low temperature vacuum oven (40° C. and $10^{-3}$ Torr). An upper electrode made of gold was formed on each of the molecular layers using a deposition apparatus maintained at −78° C. and $10^{-6}$ Torr.

EXAMPLE 13

Measurement of the Switching and Memory Characteristics of a Molecular Electronic Device The switching and memory characteristics of the molecular electronic devices manufactured in Example 12 were measured. First, the molecular electronic devices were stored and tested in a room temperature vacuum chamber to prevent deterioration due to, for example, oxidation. Current-voltage characteristic measurements were performed using a semiconductor parameter analyzer (HP 4156C, measurements ranging from 1fA/2V to 1A/200V). The switching and memory characteristics of the molecular electronic devices were measured by alternating the direction of a voltage. That is, the voltage applied to the molecular electronic devices was changed from a positive voltage (+voltage) to a negative voltage (−voltage), and, separately, from a −voltage to a +voltage, and thus the switching and memory characteristics were measured. Also, the voltage was changed 0 volts→+voltage→−voltage→+voltage to measure the switching characteristics of the device.

Figure 15:
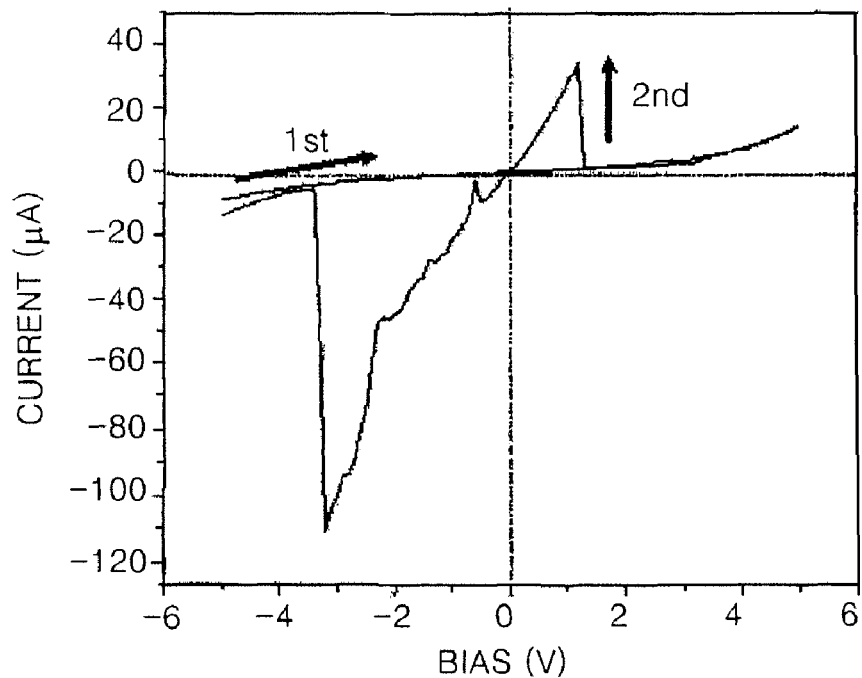
FIG. 15 is a hysteresis graph showing switching characteristics of a molecular electronic device formed using a compound according to an embodiment of the present invention.

FIG. 15 is a hysteresis graph showing switching characteristics of a molecular electronic device manufactured using the compound Ic.

The memory characteristics of the molecular electronic devices were determined by measuring a voltage pulse using a pulse generator unit (HP 41501 expander) which was connected to both the measurement apparatus and a measurement/pulse selection terminal apparatus (SMU-PGU selector, HP 16440A).

Figure 16:
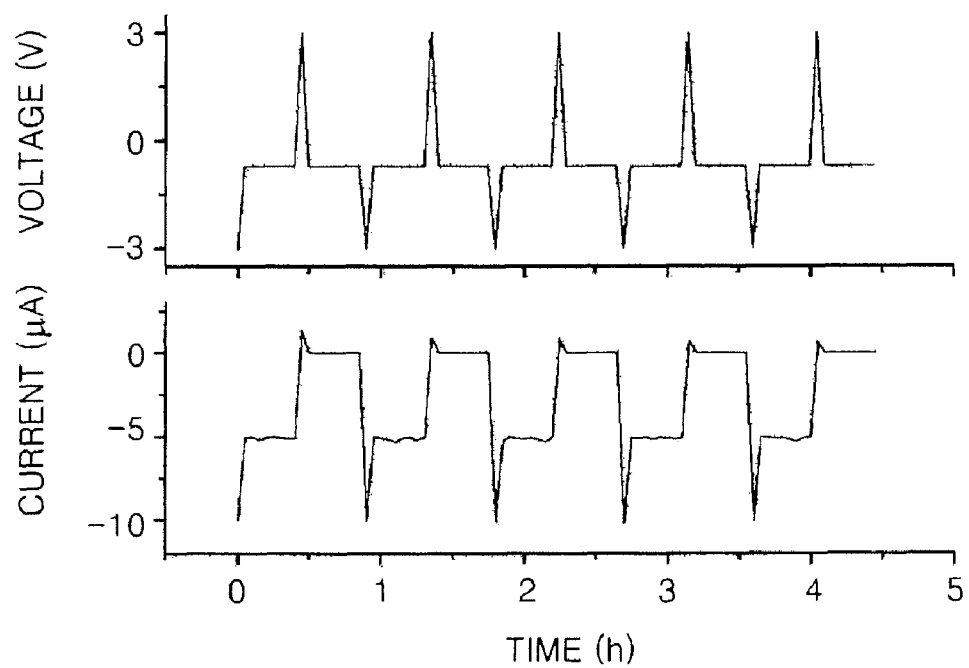
FIG. 16 is a graph showing memory characteristics of the molecular electronic device for which the hysteresis graph is shown in FIG. 15.

FIG. 16 is a graph showing memory characteristics of the molecular electronic device. In particular, the pulse generator unit generated pulses with frequencies ranging from several Hz to several MHz considering the switching characteristics of the molecular electronic devices.

The present invention provides a new electron acceptor-azo-electron donor-thiol compound derivative including an azo compound which has a dinitrothiophene group and an aminobenzene group having thiol derivatives and a method of synthesizing the compound. A molecular active layer in the form of a single molecular layer is formed on a metal electrode through self assembly from the compounds according to the present invention. Using the above-described method, a self-assembled molecular active layer formed of the compound is formed between the upper and lower electrodes, and thus a molecular electronic device having switching and memory characteristics can be formed. Since the self-assembled molecular active layer is a single molecular layer, an ultra thin nano-sized film can be formed. In addition, the thickness of the self-assembled thin film can be controlled by controlling the length of an alkyl chain in the compound according to the present invention when the compound is synthesized. In particular, the compound according to the present invention includes a thiol-based anchoring group. When employing the anchoring group, the charging effects caused by a voltage applied between two electrodes can be controlled by appropriate selection of the length and kinds of substituted molecules. That is, the magnitude of current can be controlled by the length of an alkyl group.

As described above, according to the present invention, an ultra thin molecular active layer in the form of a single molecular layer is formed on a metal electrode through self-assembly, thereby realizing a nano-sized ultra thin film device having a nano-sized microstructure.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of synthesizing a compound for forming a molecular electronic device, wherein the compound is:
   an azo compound having
   a dinitrothiophene group,
   an aminobenzene group having thiol derivatives,
      wherein the thiol derivatives are bound to the amino group, and
   an azo group directly connected between the dinitrothiophene group and para position of the aminobenzene group;
wherein the method comprising:
   forming an aminobenzene compound having thiol derivatives by reacting aniline with sulfide,
      wherein the aminobenzene compound having thiol derivatives comprises one of the following structures:

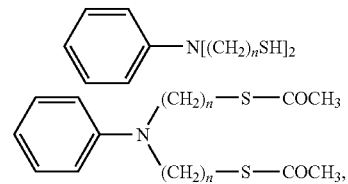

wherein n is an integer ranging from 1 to 20;
   forming a diazonium intermediate compound from 2-amino-3,5-dinitrothiophene,
   wherein the diazonium intermediate compound has the following structure:

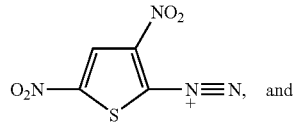

and
   azo coupling the aminobenzene compound having thiol derivatives with the diazonium intermediate compound to form an azo compound.

* * * * *